(12) United States Patent
Meriläinen et al.

(10) Patent No.: US 7,848,795 B2
(45) Date of Patent: Dec. 7, 2010

(54) DETERMINATION OF SLEEP DEPTH

(75) Inventors: Pekka Meriläinen, Helsinki (FI);
Markku Paloheimo, Espoo (FI); Juha Virtanen, Helsinki (FI); Hanna Viertiö-Oja, Espoo (FI); Petteri Lapinlampi, Espoo (FI)

(73) Assignee: General Electric Company, Schenectady, NY (US)

( * ) Notice: Subject to any disclaimer, the term of this patent is extended or adjusted under 35 U.S.C. 154(b) by 731 days.

(21) Appl. No.: 11/438,637

(22) Filed: May 22, 2006

(65) Prior Publication Data

US 2007/0270706 A1 Nov. 22, 2007

(51) Int. Cl.
*A61B 5/04* (2006.01)

(52) U.S. Cl. .................................... 600/544
(58) Field of Classification Search .......... 600/544
See application file for complete search history.

(56) References Cited

U.S. PATENT DOCUMENTS

| | | | |
|---|---|---|---|
| 5,154,180 A | 10/1992 | Blanchet et al. | |
| 5,999,846 A * | 12/1999 | Pardey et al. | 600/544 |
| 6,272,378 B1 | 8/2001 | Baumgart-Schmitt | |
| 2004/0082876 A1* | 4/2004 | Viertio-Oja et al. | 600/544 |
| 2004/0193068 A1* | 9/2004 | Burton et al. | 600/544 |
| 2005/0020934 A1 | 1/2005 | Potter et al. | |
| 2005/0137494 A1* | 6/2005 | Viertio-Oja | 600/544 |
| 2005/0190065 A1* | 9/2005 | Ronnholm | 340/575 |
| 2006/0111635 A1* | 5/2006 | Todros et al. | 600/484 |
| 2006/0135880 A1* | 6/2006 | Sarkela | 600/544 |
| 2006/0200011 A1* | 9/2006 | Suzuki et al. | 600/301 |
| 2007/0106183 A1* | 5/2007 | Suzuki et al. | 600/595 |
| 2008/0004811 A1* | 1/2008 | Suzuki et al. | 702/19 |
| 2008/0234785 A1* | 9/2008 | Nakayama et al. | 607/62 |

OTHER PUBLICATIONS

Sleigh JW, Andrzejowski J, Steyn-Ross A, Steyn-Ross J.The Bispectral Index: A Measure of Depth of Sleep, Anesth Analg 1999; 88:659-61.*
U.S. Appl. No. 11/316,374, filed Dec. 22, 2005, Viertio-Oja et al.

(Continued)

*Primary Examiner*—Patricia C Mallari
*Assistant Examiner*—Karen E Toth
(74) *Attorney, Agent, or Firm*—Andrus, Sceales, Starke & Sawall, LLP (57) ABSTRACT

The invention relates to a mechanism for determining the depth of sleep of a subject. In order to obtain information about the continuum of the depth of sleep in a user-friendly way without a need for high computational power, EEG signal data is obtained from a subject, REM sleep periods of the subject are detected, and a measure indicative of irregularity in the EEG signal data is derived. Based on the measure and the depicted REM sleep periods, a sleep depth index and state information are produced, where the index is indicative of the depth of sleep of the subject and the state information indicates whether or not the EEG signal data is obtained during a REM sleep period. The detection of the REM periods may be based on a bioimpedance measured from EEG electrodes simultaneously with the EEG measurement or on EOG signal data measured from the subject.

19 Claims, 4 Drawing Sheets

OTHER PUBLICATIONS

*A reliable probabilistic sleep stager based on a single EEG signal*, Arthur Flexer et al., Artificial Intelligence in Medicine (2005), vol. 33, pp. 199-207.

*Approximate Entropy in the Electroencephalogram During Wake and Sleep*, Naolo Burioka et al., Clinical EEG and Neuroscience, 2005, vol. 36, No. 1.

European Search Report dated Sep. 10, 2007.

Li Quanzheng et al., "Subsection Approximate Entropy and Its Application in Sleep Staging", BMES/EMBS Conference, Oct. 13-16, 1999, Atlanta, GA, 0-7803-5674-8, p. 900.

Wei-Xing et al., "Nonlinear Feature Extraction of Sleeping EEG Signals", Proceedings of the 2005 IEEE, Engineering in Medicine and Biology, 27th Annual Int'l. Conference, Shanghai, China, Sep. 1-4, 2005, 0-7803-8740-6, pp. 4614-4617.

Uchida et al., "Human Sleep Electroencephalogram Analysis Based on The Instantaneous Maximum Entropy Method", IEICE Trans. Fundamentals, vol. E80-A, No. 6, Jun. 1997, XP-000740591, pp. 965-970.

Doman et al., "Automating the sleep laboratory: implementation and validation of digital recording and analysis", Int'l. Journal of Bio-Medical Computing, Elsevier Science, Shannon, Co. Clare, IE, 38 Mar. 1995, No. 3, pp. 277-290.

\* cited by examiner

DETERMINATION OF SLEEP DEPTH

FIELD OF THE INVENTION

The present invention relates generally to sleep analysis. More particularly, the present invention relates to the determination of the depth of sleep. The depth of sleep is directly proportional to the intensity of the stimulus required to awaken the sleeper: the deeper the sleep, the more intensive the stimulus required to awaken the sleeper.

BACKGROUND OF THE INVENTION

Sleep recordings are important for the analysis, diagnosis, and treatment of various sleep disorders. Sleep staging, in turn, is a vital step in sleep analysis. Sleep staging is normally performed using the traditional Rechtschaffen & Kales (R&K) rules, which classify sleep into six separate stages: wake, rapid eye movement (REM) sleep, and S1 (light sleep) to S4 (deep sleep).

One drawback related to the traditional sleep studies is that the sleep recordings are made in separate sleep research laboratories. Due to the costly equipment involved and the trained personnel needed, the number of the laboratories is low and patients referred to a laboratory may have to travel far away. Furthermore, even though the sleep research laboratories may be comfortably furnished, many patients may find it hard to sleep naturally in these test environments.

The traditional R&K sleep staging also involves several disadvantages. First, the recording may be inconvenient for the patient due to the high number of electrodes and associated leads needed. In the traditional R&K staging, at least four channels are needed for recording an electroencephalogram (EEG), an electromyogram (EMG), and an electro-oculogram (EOG). Second, the R&K rules are insufficient and leave room for subjective interpretation. Due to this, interscorer variability is large and it is difficult to automate the staging process reliably. Third, the staging has a rather low temporal resolution, which neglects the micro-structure of sleep.

Various methods for automated sleep classification have been designed which rest on an EEG signal measured from the patient.

U.S. Pat. No. 5,154,180 discloses a method based on the correlations of the successive EEG epochs. In this method, the operator (i.e. the user) sets a threshold that affects the number of resulting classifications.

U.S. Pat. No. 6,272,378 discloses a device based on neural networks. A frontal EEG signal, measured through a three-electrode sensor, is first supplied to a hand-held device allowing the patient to perform the measurements in his or her ordinary environment. The data collected by the hand-held device is then delivered to a separate computer unit in which the data is classified by means of instructed neural networks.

The article Flexer et. al.: *A reliable probabilistic sleep stager based on a single EEG signal*, Artificial Intelligence in Medicine (2005) 33, 199-207, describes a sleep stager based on Hidden Markov models using one EEG signal. The method detects wakefulness, deep sleep, and REM sleep with an accuracy of about 80%. However, the calculations required are rather complex, which makes the device computationally expensive.

A less complex method for estimating the sleep stages based on an EEG signal is to use the entropy values of the EEG signal. As a study by Burioka et. al. shows, the values of approximate entropy decrease as the sleep gets deeper, cf. Burioka et. al.: Approximate Entropy in the Electroencephalogram During Wake and Sleep, Clinical EEG and Neuroscience, Vol. 36 No. 1, pp. 21-24. However, REM sleep causes problems since the entropy values during REM sleep correspond to those of the awake state and stage 1 non-REM sleep.

The above-described automated methods that rest on a frontal EEG signal are advantageous in the sense that the inconvenience caused to the patient/user may be reduced due to the low number of electrodes and connection wires needed. However, the methods are restricted due to the classification-based approach adopted. As the depth of the sleep is reflected only in the distinct stages determined, the current automated methods are unable to provide a clear description of the continuum of the depth of sleep. This applies especially to transitions from one sleep stage to another, which may not be abrupt changes but may take place more or less gradually.

The present invention seeks to alleviate or eliminate the above-mentioned drawbacks.

SUMMARY OF THE INVENTION

The present invention seeks to provide a novel mechanism for providing information about the continuum of the depth of sleep. The present invention further seeks to provide a mechanism which is advantageous in terms of the computational power needed and enables a user-friendly device to be implemented for sleep recordings outside sleep laboratories, especially in home environment.

In the present invention, EEG signal data is acquired from the subject. It is to be noted here that although the biopotential signal acquired from the subject is in this context termed the EEG signal, it may also include other signal components due to eye movements, eye blinks, facial muscle activity, and head movements, for example, such as a surface EEG normally does. The signal data acquired is subjected to two substantially parallel processes. In the first process, REM sleep periods of the subject are detected. In the second process, a sequence of a measure indicative of the irregularity of the EEG signal data is derived. The detected REM periods and the said sequence are then employed to produce a sleep depth index, i.e. a numeric value, indicative of the subject's sleep depth and state information indicative of whether the EEG signal data is obtained during a REM sleep period. As discussed below, the state information and the index may be employed to indicate the detected REM sleep periods as a separate REM sleep state, with or without the associated sleep depth indices.

Thus one aspect of the invention is providing a method for determining the depth of sleep of a subject. The method includes the steps of acquiring EEG signal data from a subject and detecting REM sleep periods of the subject. The method further includes the steps of deriving a measure indicative of irregularity in the EEG signal data and producing, based on the measure and the detecting step, a sleep depth index indicative of the depth of sleep of the subject and state information indicative of whether the EEG signal data is obtained during a REM sleep period.

The invention enables the sleep to be characterized by an objective and a descriptive measure termed sleep depth index in this context. The combination of the above-mentioned index and state information allows the formation of a mechanism in which the sleep depth index continuously indicates the depth of sleep during at least the non-REM sleep periods of the subject and in which the REM sleep state may be indicated separately. In this way, the user observes this special state during which the index values may behave inconsistently and assume confusing values, while a continuous measure of the depth of sleep is obtained when the index behaves consistently. Furthermore, high temporal resolution may be achieved, since the classification is omitted in the calculation of the said index. However, the index may still indicate the class/stage in question. According to the present invention, the stage of the sleep is thus reflected in the said index, rather than vice versa.

Another aspect of the invention is that of providing an apparatus for determining the depth of sleep of a subject. The apparatus includes means for acquiring EEG signal data from a subject and detection means for detecting REM sleep periods of the subject. The apparatus further includes first calculation means for deriving a measure indicative of irregularity in the EEG signal data and second calculation means, responsive to the first calculation means and the detection means, for producing a sleep depth index indicative of the depth of sleep of the subject and state information indicative of whether the EEG signal data is obtained during a REM sleep period.

A further aspect of the invention is that of providing a computer program product by means of which known patient monitoring devices may be upgraded to enable the monitor to provide information about the depth of sleep of the patient. The computer program product includes a first program code portion configured to receive EEG signal data obtained from a subject and a second program code portion configured to detect REM sleep periods of the subject. The computer program product further includes a third program code portion configured to derive a measure indicative of irregularity in the EEG signal data, and a fourth program code portion configured to determine, based on the measure and detected REM periods, a sleep depth index indicative of the depth of sleep of the subject and state information indicative of whether the EEG signal data is obtained during a REM sleep period.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 9 in the appended drawings, wherein.

DETAILED DESCRIPTION OF THE INVENTION

Figure 1:
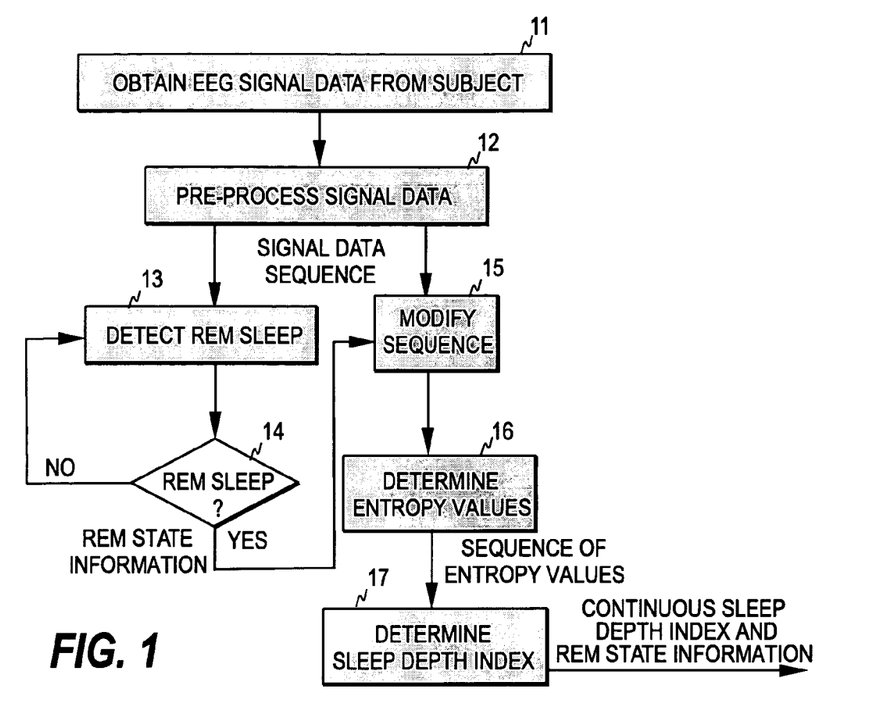
FIGS. 1 and 2 are flow diagrams illustrating, respectively, two embodiments of the method of the invention.

FIG. 1 illustrates one embodiment of the method of the present invention. As discussed above, an EEG signal is measured from a certain measurement area of the patient, such as the forehead (step 11). The measured signal is first digitized and the sampled biosignal may be filtered to exclude high- and low-frequency artifacts (step 12). As is common in the art, the digitized signal samples are processed as sets of sequential signal samples representing finite time blocks or time windows, commonly termed "epochs". The process continuously calculates the entropy values of the EEG signal data within the successive and possibly overlapping time windows (step 16). In this example, entropy refers to spectral entropy. However, instead of spectral entropy several other types of measures of irregularity may also be utilized, such as Shannon entropy or approximate entropy.

Furthermore, the process continuously monitors the incoming EEG signal data in order to detect the periods of REM sleep (step 13). If a REM period is detected (step 14/yes), the process modifies (step 15) the EEG signal data sequence input to the entropy calculation in order to add REM state information to the sequence. The modification may simply involve flagging of the signal values obtained during the REM sleep. The modification may also involve removal of the values corresponding to eye movements from the data sequence before the entropy calculation. The entropy values may then be calculated from the remaining data, i.e. from the gapped EEG data sequence. Optionally, the discarded data may be replaced by new values. This may be carried out by interpolating the new data values from non-rejected data points or by filling the gaps with predetermined constant values, such as zeroes. If the new data values do not unambiguously indicate a REM period, they may be flagged to indicate that they are obtained during REM sleep.

Based on the entropy sequence obtained from step 16, the process then determines sleep depth indices in the successive time windows (step 17). The value of the index may be scaled to a fixed range, such as between 0 and 100, using an appropriate scaling function, for example. As a result of the REM detection, the sleep depth index sequence output from step 17 is provided with state information indicative of whether or not the index values in the sequence are based on EEG signal data obtained during a REM sleep period. If no index values are produced during the REM sleep, the state information serves to indicate the periods that correspond to REM sleep. As discussed below, the index sequence may be employed to indicate the REM sleep periods with or without the index values that correspond to the REM sleep periods.

Figure 2:
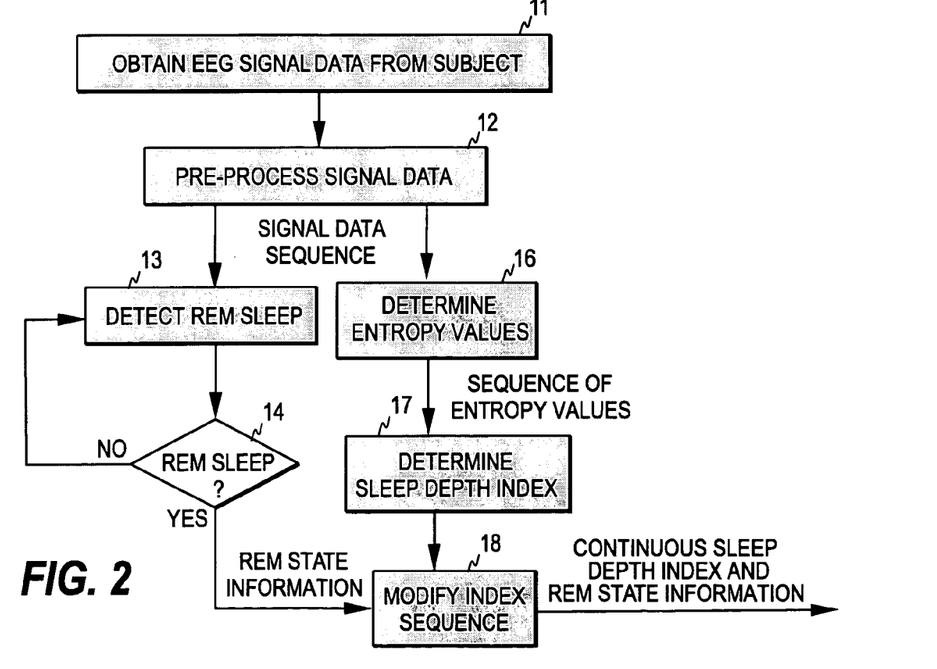

In another embodiment, which is illustrated in FIG. 2, the sleep depth index is modified during the detected REM periods to attach the REM state information to the index sequence. In this embodiment, the modification of the EEG signal data sequence (step 15 in FIG. 1) is thus omitted and the obtained sequence of the sleep depth index is modified according to the REM periods detected (step 18). The modification may simply involve flagging of the index values obtained during the REM sleep periods or replacing the respective index values with new values indicative of a REM sleep state.

Figure 3:
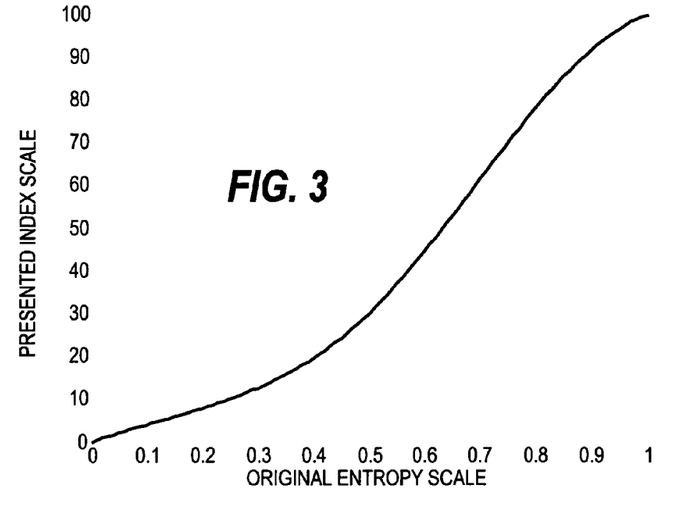
FIG. 3 illustrates an example of a scaling function utilized to map entropy values to sleep depth index values.

FIG. 3 shows an example of a scaling function, which may be employed in step 17 to map the entropy values to the index values. A relatively large portion of the original entropy scale corresponds to entropy values that do not normally occur during sleep. If spectral entropy is employed, the most interesting range of sleep depth lies between entropy values 0.5 and 1.0. Linear scaling from the original range into equidistant integer values from 0 to 100 would therefore result in a low resolution in the interesting range and in an unnecessarily high resolution in the low range. With the use of a nonlinear, e.g. a spline, function in the transform the resolution of the measurement may be enhanced in the interesting region of the original entropy scale.

The detection of the REM sleep periods may be based on a separate biosignal measurement or on the analysis of the measured EEG data sequence. Different methods for detecting the REM sleep are discussed below.

Figure 4:
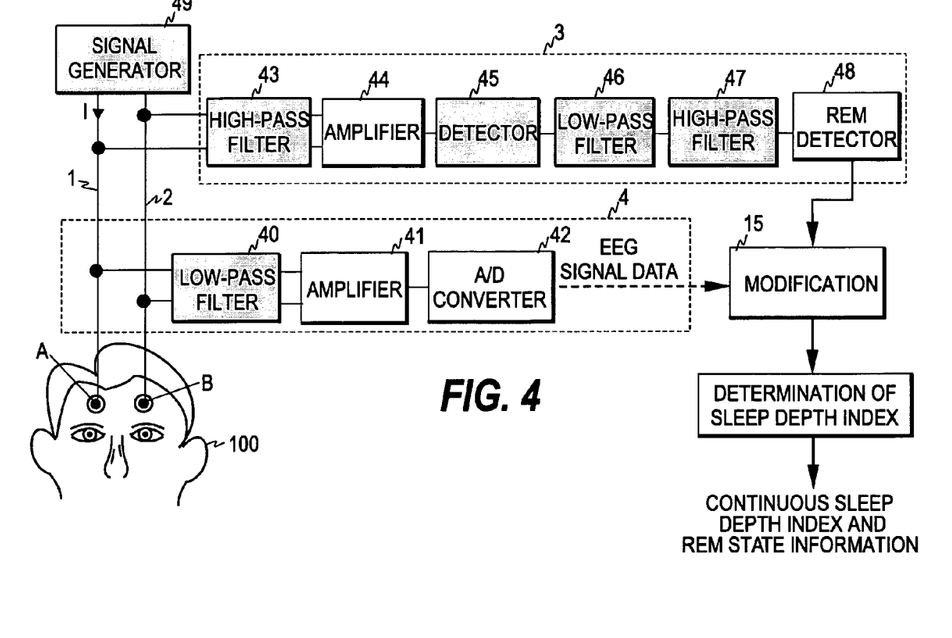
FIG. 4 illustrates an embodiment of the invention, in which the detection of REM sleep is based on a bioimpedance measurement.

In one embodiment of the invention, which is illustrated in FIG. 4, the detection of REM sleep is based on a bioimpedance measurement performed simultaneously with the EEG measurement. When applied to human facial areas, bioimpedance measurement provides information about blood flow, eye movements, and eye blinks, which affect the volume conduction properties.

As is shown in FIG. 4, active electrodes A and B of an EEG measurement are attached in the facial area of a patient 100, preferably onto the forehead of the patient. The EEG signal obtained from the electrodes is directed to an EEG measurement branch 4 comprising a low-pass filter 40 at its front end.

Figure 5A:
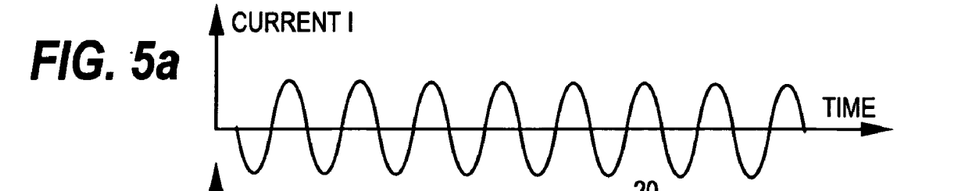
FIGS. 5a to 5d illustrate the measured bioimpedance signal in different points of the impedance measurement branch of the apparatus of FIG. 4.

In the embodiment of FIG. 4, the excitation signal of the bioimpedance measurement is fed to the same electrodes from which the EEG signal is acquired. For supplying the excitation signal, the apparatus includes a signal generator 49 connected to electrodes A and B through corresponding wires 1 and 2. The frequency of the excitation signal supplied to the patient is well above the EEG signal band, typically in the range of 20-100 kHz, in order to enable continuous and simultaneous bioimpedance measurement that does not interfere with the EEG measurement. FIG. 5a illustrates the excitation signal output from the signal generator.

The impedance signal is measured from the same electrodes by connecting an impedance measurement branch 3 to wires I and 2. The impedance measurement branch includes a high-pass filter 43 at its front end.

The low-pass filter 40 of the EEG measurement branch prevents high frequencies, i.e. the excitation signal, from entering the EEG measurement branch, while the high-pass filter 43 prevents the low frequencies, i.e. the EEG signal, from entering the impedance measurement branch.

In the measurement branches the filtered signals are first amplified; the EEG signal is supplied to an amplifier 41 of the EEG measurement branch, while the impedance signal is supplied to an amplifier 44 of the impedance measurement branch. The amplifiers are typically differential amplifiers.

The EEG measurement branch further includes an A/D converter 42 that samples the EEG signal and converts it into digitized format. The A/D converter thus outputs a sequence of EEG signal data. After the low-pass filter 40, the EEG signal is processed in a conventional manner to obtain the said sequence.

Figures 5B, 5C:
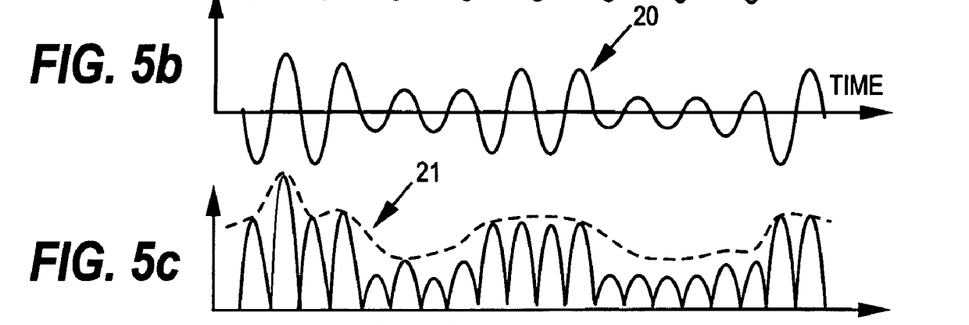

In the 2-lead configuration of FIG. 4, the signal generator supplies an excitation current I to the patient. The voltage between the electrodes, i.e. the signal measured by the impedance measurement branch, is then proportional to the impedance of the signal path formed between electrodes A and B. At this stage, the frequency content of the measured signal is concentrated around the frequency of the excitation current. FIG. 5b illustrates the impedance signal 20 output from amplifier 44. As can be seen, impedance changes cause slow changes in the signal.

In order to analyze the impedance changes over time, the impedance signal is typically demodulated in a detector 45 using the excitation frequency. This produces a time-varying signal indicating how the impedance of the signal path varies over time. As is shown in FIG. 5c, the detector typically outputs an impedance signal 21, which corresponds to the envelope of the rectified input signal 20 and varies slowly over time in accordance with the impedance changes. This signal is then typically low-pass filtered in a first filter 46 in order to reduce noise and further high-pass filtered in a second filter 47 to remove the often uninteresting DC component and low-frequency fluctuation.

Figure 5D:
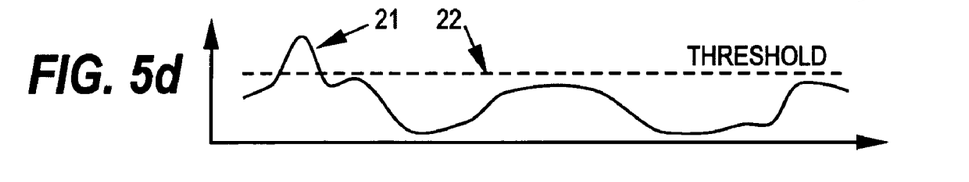

The filtered impedance signal is then supplied to a REM detector 48, which compares the impedance signal 21 with a predetermined threshold 22, as is illustrated in FIG. 5d, and determines the time periods during which the impedance signal exceeds the threshold. These periods are regarded as REM sleep periods and the temporal location of the periods is utilized to modify the EEG signal data sequence (as in FIG. 4) or the sleep depth index sequence. This is performed in a modification unit 15. As noted above, the DC value of the impedance signal is typically removed, in which case the alternating component of the impedance is compared with the threshold.

It is also possible to use an excitation frequency, which is at or close to the EEG frequency band. In this case both the EEG signal and the impedance signal may be amplified and digitized as one composite signal and the rest of the above-described steps may be implemented as software algorithms.

As noted above, the bioimpedance measurement provides information about blood flow and thus includes a periodic component at a frequency corresponding to the pulse rate of the patient. Since the said component represents artifact from the point of view of the detection of eye movements (i.e. REM periods), the said pulsating component may be removed from the impedance signal in one embodiment of the invention. This may be performed in high-pass filter 47 or in a separate removal unit before or after the high-pass filter, for example.

The bioimpedance measurement of FIG. 4 provides a user-friendly measurement arrangement, since only two electrodes with associated leads are needed.

In another embodiment of the invention, the detection of REM sleep may be based on separate electro-oculographic (EOG) and EEG signals (channels). The EOG signal may be obtained using separate EOG electrodes or an electrode array designed for uncoupling the EEG and the EOG signals.

Figure 6:
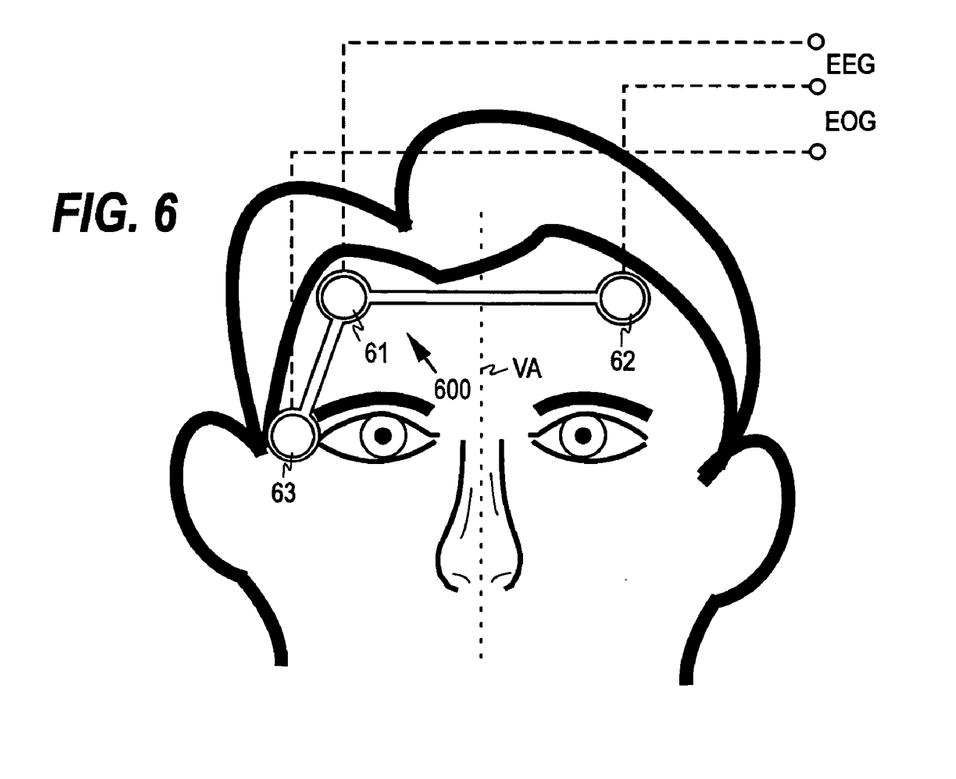
FIG. 6 illustrates one embodiment of an electrode configuration for measuring EEG and EOG signal data simultaneously.

FIG. 6 illustrates an electrode configuration 600 that enables efficient detection of eye movements with a minimum number of electrodes. The electrode configuration comprises three measurement electrodes 61 to 63 of which the first and second electrodes are for measuring the EEG signal and the third and second electrodes for measuring the EOG signal. The first electrode 61 is positioned onto the hairless fronto-lateral area of the frontal lobe of the patient, preferably as far as possible from the eye. The second measurement electrode 62 is positioned similarly as the first measurement electrode, but on the opposite cortical hemisphere of the patient. Furthermore, the first and second electrodes are positioned substantially horizontally (i.e. in the same horizontal line) and at substantially equal distances from the vertical center axis VA of the face, i.e. the second measurement electrode is positioned onto the spot which is the mirror image of the spot of the first measurement electrode, and vice versa, the vertical center axis being the mirror axis.

The EEG signal is measured from the first and second measurement electrodes 61 and 62. Due to the symmetrical positions of the electrodes, the potential changes caused by vertical eye movements are substantially the same at both electrodes (assuming that the eyes move similarly to each other, as is the case normally). In other words, the potential changes caused by vertical eye movements tend to cancel in the EEG signal, which the voltage difference of the electrodes represents. However, the EEG channel remains sensitive to horizontal eye movements. In the embodiment of FIG. 6, the third measurement electrode 63 and one of the first and second measurement electrodes are employed to measure the EOG signal. For this purpose, the third measurement electrode is positioned so that the EOG voltage measured between this electrode and one of the first and second electrodes is as high as possible in case of horizontal movement of the eyes. In the example of FIG. 6, the said one electrode is the second measurement electrode 62, i.e. the EOG voltage is measured between electrodes 63 and 62. Therefore, the third measurement electrode is positioned on the temple of the patient, on the hemisphere opposite to that of measurement electrode 62. The temple here refers to the area between an eye and the ear on the same hemisphere as the eye. As to their internal structure, the electrodes may be similar to each other. Various other electrode configurations that enable the detection of eye movements with a minimum number of electrodes are disclosed in U.S. patent application Ser. No. 11/316,374.

For each epoch, the EOG signal may be utilized to detect eye movements and related REM periods. This may be done, for example, by examining whether the absolute value of any of the EOG signal values within an epoch exceeds a predetermined threshold value. Alternatively, the EEG and EOG signals may be compared with each other in order to detect the REM periods. This may be done, for example, by determining the difference of the absolute values of simultaneous EOG and EEG signal values for each sample in an epoch ($|S_{EOG}(t_i)|-|S_{EEG}(t_i)|$). It may then be examined whether any of the differences exceeds a predetermined threshold. If this is the case, the entropy or index value corresponding to the epoch is flagged or modified to indicate that REM sleep is involved.

In a further embodiment, an electromyographic (EMG) signal may be used to further rule out periods of high EOG activity during which the patient is not asleep. Since EMG activity is at its minimum during REM sleep, the EMG channel may be used to indicate when REM sleep is not involved even though the comparison with the threshold indicates REM sleep. Thus in this embodiment the entropy or index value corresponding to an epoch is flagged or modified, if any of the above absolute values or differences in the epoch exceeds the associated threshold and if the EMG value is simultaneously below a respective threshold indicating that the patient is asleep.

Figure 7:
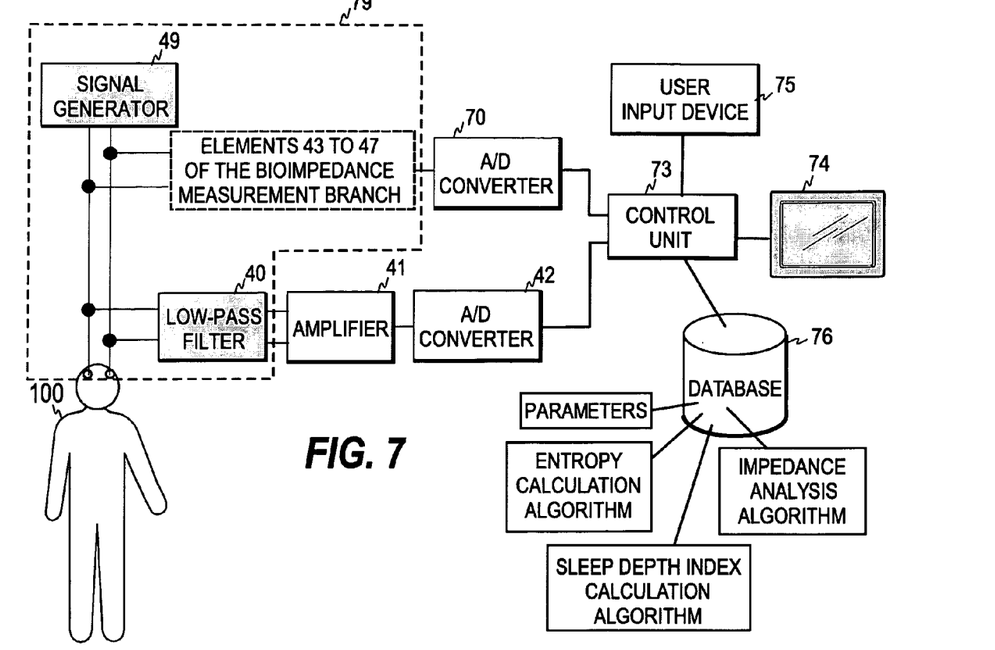
FIG. 7 illustrates one embodiment of the apparatus/system of the invention.

FIG. 7 illustrates one embodiment of the system or apparatus according to the invention. It is assumed here that the detection of REM sleep is based on the bioimpedance measurement shown in FIG. 4. Similar elements have been provided with the same reference numbers as above, and elements 43 to 47 of FIG. 4 are denoted with one block. In this embodiment, the digitized EEG signal data is supplied to a control unit 73 which may comprise one or more computer units or processors. The impedance signal output from high-pass filter 47 is converted into digitized format in an A/D converter 70, which supplies the digitized impedance signal to the control unit. In this embodiment, the control unit thus takes over the role of the REM detector 14. In other words, the control unit compares the impedance signal with the predetermined threshold and detects the REM periods in the EEG signal data. Based on the EEG signal data sequence, the control unit further calculates the entropy value sequence and the sleep depth index sequence. Depending on the embodiment, the control unit may flag or modify the EEG sequence or the sleep depth index sequence based on the detected REM periods.

The control unit is provided with a memory or database 76 holding the digitized EEG data and the digitized impedance data. The memory or database may also store the algorithm for analyzing the impedance data, various parameters needed in the REM detection, such as the threshold value with which the impedance signal is compared, and the calculation algorithms for calculating the entropy values and the sleep depth indices.

Figure 8:
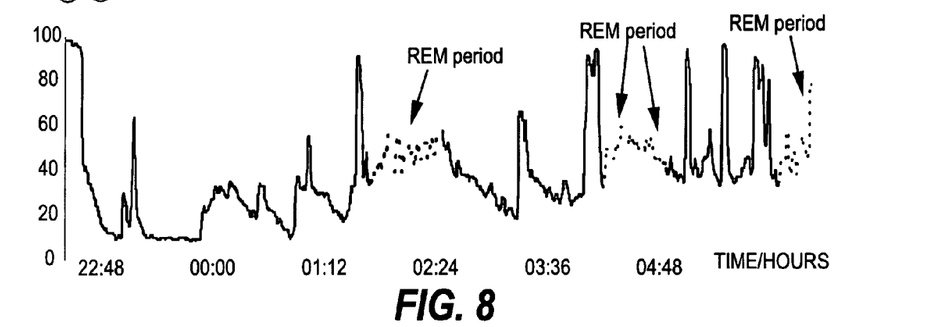
FIGS. 8 and 9 illustrate different display modes of the apparatus of the invention.

The sleep depth index signal may then be displayed on the screen of a monitor 74, which forms part of the user interface of the apparatus/system. As is shown in FIG. 8, the index sequence may be flagged to indicate the REM periods. In this display mode, the REM segments of the sleep depth index curve are thus marked to allow the user to distinguish the REM segments from the sequence. The REM segments may be indicated, for example, by using a different color for the sleep depth index curve during the REM periods.

Figure 9:
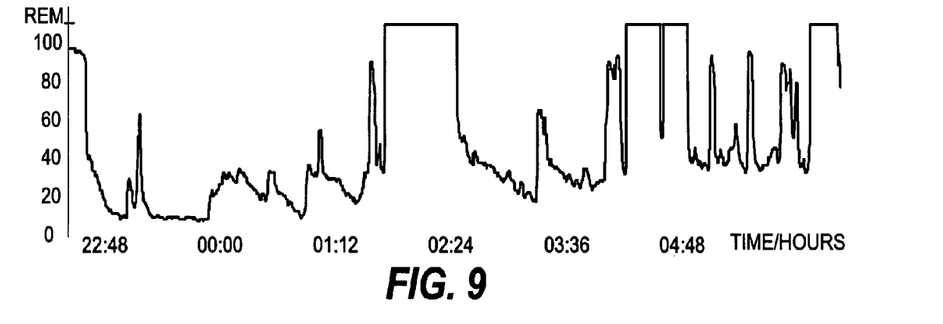

In another display mode, shown in FIG. 9, the REM periods are shown as a separate REM state which is outside the value range of the sleep depth index. The display mode of the apparatus may be selected independently of whether the embodiment of FIG. 1 or 2 is in question.

Although a control unit comprising one computer unit or one processor may perform the above steps, the processing of the data may also be distributed among different units/processors (servers) within a network, such as a hospital LAN (local area network). The apparatus of the invention may thus also be implemented as a distributed system.

The user may control the operation of the apparatus/system through a user input device 75, such as a keyboard. As discussed above, the bioimpedance measurement elements, denoted with reference number 79, may also be replaced by EOG measurement elements for detecting the REM and non-REM sleep periods. In this case the control unit may thus determine, for example, the difference of the absolute values of simultaneous EOG and EEG signal values for each sample in an epoch or the highest absolute EOG signal value in an epoch, and examine, respectively, whether any of the differences or the said highest absolute value exceeds the respective threshold. If this is the case, the control unit flags or modifies the EEG signal values or the index value corresponding to the epoch to indicate that REM sleep is involved.

A patient monitor in which EEG data and continuous bioimpedance or EOG data are available may also be upgraded to enable the monitor to provide information about the depth of sleep of the patient. Such an upgrade may be implemented by delivering to the patient monitor a software module that enables the device to detect the REM periods and determine the sleep depth index sequence in the above-described manner. The software module may be delivered, for example, on a data carrier, such as a CD or a memory card, or through a telecommunications network. The software module may be provided with interfaces for receiving EEG and impedance/EOG data. The software module then performs, utilizing the impedance/EOG data available, the above-described REM detection and outputs a modified or flagged index sequence in which the REM sleep periods are indicated. The software module may receive the EEG and bioimpedance/EOG signals in real-time directly from the electrodes of the monitor or from the memory of the patient monitor after the actual measurement. In the latter case, the signals may already be temporally aligned by time stamps attached to the signal values. As also discussed above, the EOG data may be associated with EMG data to rule out periods of high EOG activity during which the patient is not asleep.

Although the invention was described above with reference to the examples shown in the appended drawings, it is obvious that the invention is not limited to these, but may be modified by those skilled in the art without departing from the scope of the invention. For example, instead of the EEG data sequence or the index sequence the REM sleep periods of the entropy sequence may also be modified or flagged to indicate that REM sleep is involved. Instead of a continuous index sequence, the mechanism of the invention may also be employed to determine distinct index values provided with REM state information.

The invention claimed is:

1. A method for determining the depth of sleep of a subject, the method comprising the steps of:
   acquiring EEG signal data from a subject;
   detecting REM sleep periods of the subject from the EEG signal data using a control unit;
   deriving a sequence of a measure indicative of irregularity in the EEG signal data using the control unit;
   producing, based on the measure and the detecting step, a combined sleep depth curve depicting both a sequence of a sleep depth index indicative of the depth of sleep of the subject and state information indicative of whether the EEG signal data is obtained during a REM sleep period;
   discarding selected segments of the EEG signal data, the selected segments corresponding to the REM sleep periods detected in the detecting step; and
   displaying the combined sleep depth curve on a monitor, wherein the portions of the combined sleep depth curve obtained during the REM sleep periods are visually distinguished from other sleep periods.

2. A method according to claim 1, wherein the detecting step includes the sub-steps of:
   supplying an AC excitation signal through a signal path formed between two electrodes of an electrode set attached to the subject's skin surface in a measurement area of the subject's body;
   measuring an impedance signal through the electrode set, the impedance signal being indicative of the impedance of the signal path;
   determining at least one time period during which the impedance signal fulfills at least one predetermined criterion; and
   defining the REM sleep periods based on the at least one time period.

3. A method according to claim 2, wherein the determining sub-step includes a sub-step of comparing the impedance signal with a predetermined threshold value.

4. A method according to claim 1, further comprising a step of replacing the selected segments with new signal values.

5. A method according to claim 1, wherein the deriving step includes deriving the measure indicative of irregularity in the EEG signal data, in which the measure is indicative of spectral entropy of the EEG signal data.

6. A method according to claim 1, wherein the detecting step includes the sub-steps of:
   acquiring EOG signal data from the subject; and
   utilizing the EOG signal data for defining the REM sleep periods.

7. A method according to claim 6, wherein the utilizing sub-step includes comparing the EOG signal data with a predetermined threshold.

8. A method according to claim 6, wherein the utilizing sub-step includes comparing the EOG signal data with the EEG signal data.

9. An apparatus for determining the depth of sleep of a subject, the apparatus comprising:
   means for acquiring EEG signal data from a subject;
   detection means for detecting REM sleep periods of the subject;
   first calculation means for deriving a sequence of a measure indicative of irregularity in the EEG signal data; and
   second calculation means, responsive to the first calculation means and the detection means, for producing a combined sleep depth curve depicting both a sequence of a sleep depth index indicative of the depth of sleep of the subject and state information indicative of whether the EEG signal data is obtained during a REM sleep period, wherein the REM sleep periods are visually distinguished from other sleep periods in the combined sleep depth curve,
   wherein the first calculation means are configured to discard selected segments of the EEG signal data, the selected segments corresponding to the REM sleep periods detected by the detection means.

10. An apparatus according to claim 9, wherein the detection means comprise:
    signal generator means for supplying an AC excitation signal through a signal path formed between two electrodes of an electrode set when said set is attached to a subject's skin surface in a measurement area of the subject's body;
    impedance measurement means for measuring an impedance signal through the electrode set, the impedance signal being indicative of the impedance of the signal path;
    first means for determining at least one time period during which the impedance signal fulfills at least one predetermined criterion; and
    second means for defining the REM sleep periods based on the at least one time period.

11. An apparatus according to claim 10, wherein the first means are configured to compare the impedance signal with a predetermined threshold value.

12. An apparatus according to claim 9, wherein the first calculation means are further configured to replace the selected segments with new signal values.

13. An apparatus according to claim 9, wherein the second calculation means are configured to convert values in the sequence of the measure to a predetermined value range, thereby to obtain the sequence of the sleep depth index.

14. An apparatus according to claim 13, further comprising display means for displaying the sequence of the sleep depth index for non-REM sleep periods and for indicating, based on the state information, the REM periods as a separate REM sleep state distinct from the predetermined value range.

15. An apparatus according to claim 13, further comprising display means for displaying the sequence of the sleep depth index for the REM and non-REM sleep periods and for expressing, based on the state information, the sequence differently for the REM and non-REM periods.

16. An apparatus according to claim 9, wherein the measure indicative of irregularity in the EEG signal data is indicative of spectral entropy of the EEG signal data.

17. An apparatus according to claim 9, further comprising means for acquiring EOG signal data from the subject.

18. An apparatus according to claim 17, wherein the detection means are configured to define the REM sleep periods based on the EOG signal data.

19. An apparatus according to claim 17, wherein the detection means are configured to define the REM sleep periods based on the EOG signal data and the EEG signal data.

* * * * *

UNITED STATES PATENT AND TRADEMARK OFFICE
CERTIFICATE OF CORRECTION

| | |
|---|---|
| PATENT NO. | : 7,848,795 B2 |
| APPLICATION NO. | : 11/438637 |
| DATED | : December 7, 2010 |
| INVENTOR(S) | : Meriläinen et al. |

It is certified that error appears in the above-identified patent and that said Letters Patent is hereby corrected as shown below:

On the Title Page, in Item (57), under "ABSTRACT", in Column 2, Line 8, delete "depicted" and insert -- detected --, therefor.

In Column 5, Line 30, delete "I" and insert -- 1 --, therefor.

Signed and Sealed this
Twenty-sixth Day of April, 2011

David J. Kappos
*Director of the United States Patent and Trademark Office*